(12) United States Patent
Blanloeil et al.

(10) Patent No.: US 10,086,185 B2
(45) Date of Patent: Oct. 2, 2018

(54) ACCESS PORT

(71) Applicant: B. Braun Medical SAS, Chasseneuil (FR)

(72) Inventors: Patrick Blanloeil, Fontaine-le-Comte (FR); Cyril Prudhomme, Cambrai (FR)

(73) Assignee: B. Braun Medical SAS, Chasseneuil (FR)

( * ) Notice: Subject to any disclaimer, the term of this patent is extended or adjusted under 35 U.S.C. 154(b) by 66 days.

(21) Appl. No.: 14/848,753

(22) Filed: Sep. 9, 2015

(65) Prior Publication Data

US 2016/0074647 A1    Mar. 17, 2016

(30) Foreign Application Priority Data

Sep. 15, 2014 (EP) .................................. 14184763

(51) Int. Cl.
*A61M 39/02* (2006.01)
*A61M 39/04* (2006.01)
(Continued)

(52) U.S. Cl.
CPC ........ *A61M 39/0208* (2013.01); *A61M 39/04* (2013.01); *B29C 45/14073* (2013.01);
(Continued)

(58) Field of Classification Search
CPC .............. A61M 39/0208; A61M 39/02; A61M 2039/0202; A61M 5/14276; A61M 2039/0205; A61M 2039/0276; A61M 2039/0226; A61M 2039/0223; A61M 2039/0238; A61M 39/0247; A61M 39/0202; A61M 39/0205; A61M 2039/0288; A61M 2039/0294; A61M 2039/0261; A61M 2039/027; A61M 2039/0279
See application file for complete search history.

(56) References Cited

U.S. PATENT DOCUMENTS 4,802,885 A    2/1989 Weeks
4,904,241 A *  2/1990 Bark ................. A61M 39/0208
                                                604/117
(Continued)

FOREIGN PATENT DOCUMENTS

DE    3628337    5/1988
EP    1736196    12/2006
(Continued)

OTHER PUBLICATIONS

European Search Report dated Jan. 9, 2015 for European Application No. 14184763.2.

*Primary Examiner* — Emily Schmidt
*Assistant Examiner* — Alexandra Lalonde
(74) *Attorney, Agent, or Firm* — RatnerPrestia

(57) ABSTRACT

An access port includes a molded housing portion forming a reservoir for receiving fluid. The housing portion includes a shielding plate arranged on an inner base of the housing portion; an open end in which a septum is arranged; an exit passage; and a wall, the shielding plate including a circular portion having a periphery. The lower side and the periphery of the shielding plate are embedded into the housing portion. Furthermore, a shielding plate is insert molded into the housing portion.

6 Claims, 6 Drawing Sheets

(51) Int. Cl.
 *B29C 45/14* (2006.01)
 *B29K 101/00* (2006.01)
 *B29L 31/00* (2006.01)

(52) U.S. Cl.
 CPC ............... *A61M 2039/0202* (2013.01); *A61M 2039/0205* (2013.01); *A61M 2039/0226* (2013.01); *A61M 2207/00* (2013.01); *B29K 2101/00* (2013.01); *B29L 2031/753* (2013.01)

(56) References Cited

U.S. PATENT DOCUMENTS

| | | | |
|---|---|---|---|
| 5,213,574 A * | 5/1993 | Tucker | A61L 29/02 424/423 |
| 6,527,754 B1 * | 3/2003 | Tallarida | A61M 39/0208 604/288.02 |
| 8,021,324 B2 | 9/2011 | Bizup | |
| 8,029,482 B2 | 10/2011 | Maniar | |
| 8,075,536 B2 | 12/2011 | Gray | |
| 8,202,259 B2 | 6/2012 | Evans | |
| 2007/0010790 A1 * | 1/2007 | Byrum | A61M 39/0208 604/288.02 |

FOREIGN PATENT DOCUMENTS

| | | | |
|---|---|---|---|
| EP | 2441490 | 4/2012 | |
| EP | 2441490 A1 * | 4/2012 | ........ A61M 39/0208 |

\* cited by examiner

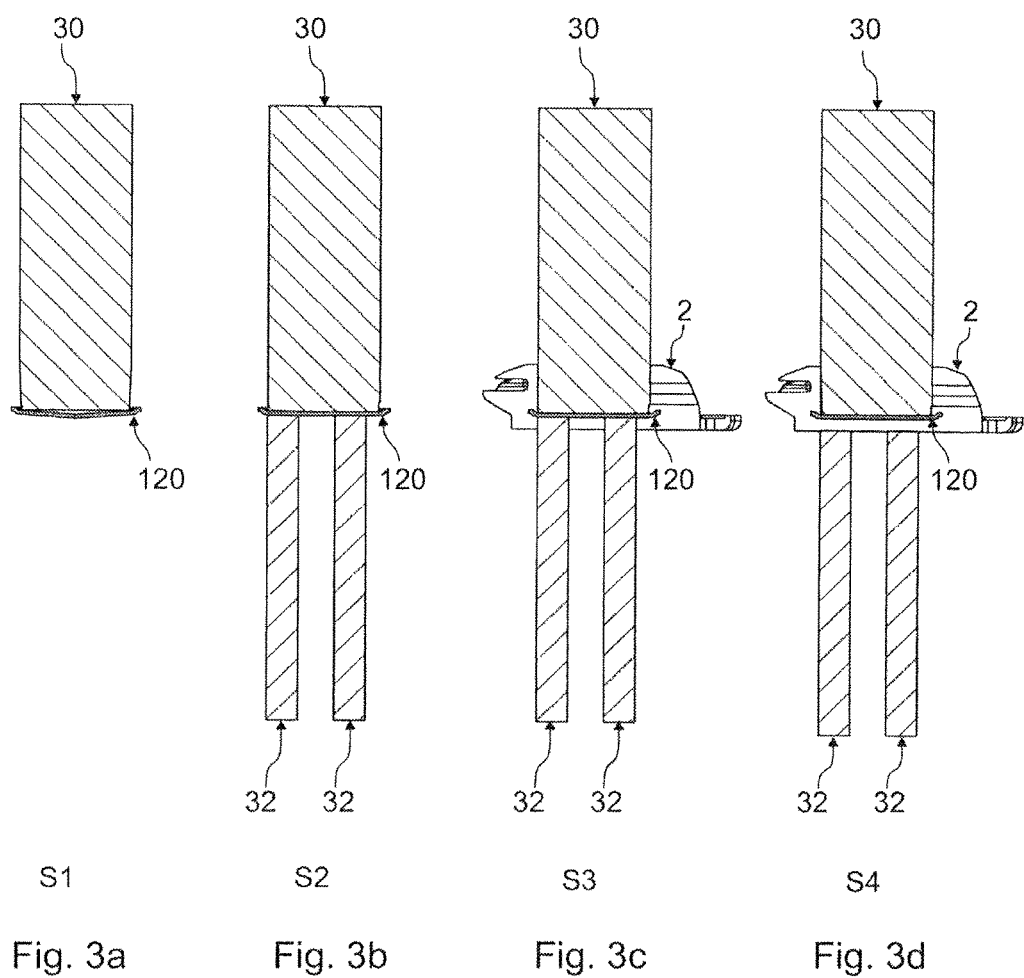

ACCESS PORT

RELATED APPLICATIONS

This application claims the benefit of priority under 35 U.S.C. § 119 of European Application No. EP 14 184 763.2, filed Sep. 15, 2014, the content of which is incorporated herein by reference in its entirety.

FIELD OF THE INVENTION

The invention relates generally to an access port, and more particularly to an access port having a housing portion and reservoir for receiving fluid.

BACKGROUND

In the administering and/or withdrawal of fluids from a patient, an access port is often used comprising a reservoir having on one end a self-sealing septum through which a needle is insertable. The reservoir further comprises an exit passage fluidly connected to a cannula. After surgically implanting the access port in the patient such that the septum is positioned subcutaneously, and attaching the other end of the cannula to a catheter inserted into an internal part of the body (typically a vein), fluids can be administered and/or blood samples taken through the insertion of a (typically non-coring) needle into the reservoir via the septum. Thus in the case of administering a fluid, said fluid flows through the needle, into the access port and through the attached cannula. In this way repeated access to the inside of patient is facilitated. In conventional access ports the reservoir may be made from metal or plastic.

When the needle is inserted through the septum, the resistance is quite high (around 8 N). In order for a medical professional to ensure that the needle has completely traversed the septum, allowing the needle bevel opening to be exposed beneath the septum, he or she must feel that the needle is touching the base of the reservoir of the port. This requires that he/she feels that the needle can no longer advance. If the internal base of the reservoir is made from a soft material, the needle will mark the internal base of the reservoir.

Access ports having a plastic reservoir and metal base are known from prior art.

For example an access port is known from U.S. Pat. No. 6,527,754 B1 comprising a housing made from molded plastic, an exit passage and a septum. The internal base of the housing is formed from a metallic shielding plate having a bent rim portion, which is molded or bonded to the housing. The metallic shielding plate, housing and septum define a reservoir.

In the access port according to U.S. Pat. No. 6,527,754 B1, the metallic shielding plate is fixed to the housing only at the rim portion. The shielding plate can come loose from the housing due to the forces that result from repeated needle insertions and other forces during operation. In other words the retention of the metallic shielding plate can be compromised which can lead to loss of sealing between the housing and shielding plate, and in the worst case detachment of the metallic shielding plate from the housing. Therefore it is a problem in the case of ports having a plastic housing and metal shielding plate that the shielding plate does not remain leak free or even can come loose from the housing.

SUMMARY OF THE INVENTION

It is an object of the invention is to provide an access port having a one-piece plastic housing, that comprises a shielding plate that is firmly anchored to the housing.

A further object of the invention is to provide a method for insert molding the shielding plate of an access port into the housing.

This object is solved by an access port according to claim 1. Advantageous further developments of the access port arise from the dependent claims.

The access port according to the invention has a molded housing portion. The housing portion may be a lower housing portion which can be connected to an upper housing portion so as to form the access port. The housing portion may also be a single-unit molded housing of the access port. The housing portion forms a reservoir for receiving fluid, said reservoir comprising: a shielding plate arranged on an inner base of the housing portion; an open end in which a septum is arranged; an exit passage, and a wall. The wall is preferably tapered.

According to the invention, "upper" side or surface is defined as the respective side or surface facing from the inner base in the direction of the open end of the reservoir, and "lower" side or surface is defined as the respective side or surface facing in the opposite direction to the upper side. Furthermore "axial direction" is defined as a direction parallel to the axis of revolution of the reservoir surface ("axis of the reservoir"), and "lateral direction" is a direction normal and away from said axis.

The shielding plate comprises a circular portion which has a periphery. The lower side and the periphery of the shielding plate are embedded into the housing portion.

By means of the embedding of both the lower side of the shielding plate and the periphery of the circular portion into the housing portion, it is achieved that the shielding plate is firmly anchored to the inner base of the housing portion. The likelihood of lateral displacement of the shielding plate or detachment of the shielding plate from the housing portion due to the force of an inserted needle is reduced.

The shielding plate may be either metallic or ceramic. In this way the shielding plate is made from a hard material and so is not damaged by needle insertions. Preferably the shielding plate is made from titanium or stainless steel.

The shielding plate may be bonded to the housing portion and/or insert molded into the housing portion. In this way the shielding plate is firmly fixed to the housing portion.

The shielding plate may have an annular region embedded on all of its sides into the housing portion. In this way the shielding plate is firmly anchored to the housing portion and leakage of fluid in between the shielding plate and housing portion is prevented, that is to say the connection between the housing portion and the shielding plate is well sealed.

A bent portion having an axially extending portion embedded on all of its sides into the housing portion may be formed on the annular region. In this way the shielding plate may be even more firmly anchored to the housing portion. The axial extending portion creates a form-locking connection between the shielding plate and the housing portion. In this way displacement of the shielding plate, in particular lateral displacement of the shielding plate, is further reduced. In addition, the bent portion may be used to position the shielding plate onto the corepin of a mold tool for insert molding the shielding plate into the housing portion. Here the bent portion may have an inner dimension suitably sized to fit around the outer diameter of the lower face of the first corepin. In this way the accuracy of the positioning of the shielding plate relative to the housing portion can be increased, and lateral movement of the shielding plate during molding can also be reduced.

The bent portion may be formed all around the annular region. In this way the shielding plate is more firmly anchored to the housing portion.

The bent portion may comprise at least one extension extending from a portion of the annular region. Preferably the extension is embedded on all of its sides into the housing portion. In this way the anchoring of the shielding plate to the housing portion is further ensured. In addition the shielding plate can be easily designed or oriented so as not to obstruct the exit passage of the access port.

The at least one extension may be directed parallel to the axis of the reservoir. In this way the anchoring of the shielding plate to the housing portion is further ensured. Preferably a plurality of extensions are provided to position the shielding plate onto the corepin of a mold tool used to insert mold the shielding plate into the housing portion. Here the extensions have an inner dimension suitably sized to fit around the outer diameter of the lower face of the first corepin. In this way the accuracy of the positioning of the shielding plate relative to the housing portion may be increased. Preferably the number of extensions is three and further preferably the extensions are equispaced around the periphery of the circular portion.

The at least one extension may be inclined towards or away from the axis of the reservoir. In the preferable case that the extension is inclined towards the axis of the reservoir, it is possible to increase the plastic wall thickness of the wall on the radially inner side of each the extension, in an axial direction from the open end towards the reservoir. Thus the wall strength of the access port is increased at the inner base end. The angle can be chosen so that the extension, in particular the upper end of the extension, avoids interfering with other features of the access port. In order to achieve this, and in the case of more than one extension being provided, the respective angle of each extension may be chosen independently.

The at least one extension may extend along the entire axial length of the wall. In this way the anchoring of the shielding plate to the housing portion may be further ensured. In a modification of the above-mentioned preferred configuration in which a plurality of extensions, further preferably three extensions, are provided, the extensions may be resiliently laterally deformable and sized so as to be biased against the cylindrical surface of the corepin. As a result, axial alignment of the shielding plate relative to the housing portion is improved since the lateral clearance between the corepin and the extensions is removed. Lateral movement of the shielding plate during the molding process is advantageously reduced. Preferably an orientation of the shielding plate is chosen such that none of the extensions obstructs the exit passage.

According to an exemplary embodiment, at least one recess is formed on the circular portion laterally beyond at least one extension, preferably beyond each of the at least one extension. In this way the plastic material of the wall is allowed to extend axially through each recess. As a result, uninterrupted reinforcing portions of the molded wall can be provided, and so the wall is not excessively weakened by the embedding of part of the circular portion. Additionally the diameter of the circular portion may be optimized independently of the lateral extent of the at least one extension. In other words the choice of diameter of the circular portion is unconstrained by the positional requirements of the long extension. In a preferable configuration at least one recess is provided laterally beyond each of the at least one extensions.

The diameter of the maximum periphery of the circular portion may preferably be greater than the maximum internal diameter of the reservoir. In this way the shielding plate may be more firmly anchored to the housing portion. In particular axial displacement of the shielding plate may be further prevented.

According to another exemplary embodiment, the upper side of the circular portion may be concave. This configuration brings the advantage that during insert molding, surface pressure can be applied from the corepin of a mold tool predominantly over a laterally outer annular surface of the upper face of the shielding plate. In this way leakage of liquid plastic into the reservoir during the molding process is prevented. The concave surface may be conical or dome-shaped (spherical) for example.

The above-mentioned extensions including the preloading of the curved or concave shielding plate all prevent and/or limit the amount of movement possible of the plate during injection of the liquid plastic into the mold.

According to an aspect of the invention, the access port may have an upper housing portion and a lower housing portion being connected to each other with the septum arranged therebetween, wherein the shielding member is embedded into the lower housing portion of the access port.

According to an alternative aspect of the invention the access port may have a single-unit molded housing.

Another aspect of the invention provides a method for insert molding the shielding plate into the housing portion of the access port, comprising: in a first step positioning the shielding plate preferably concentrically over a first corepin of a mold tool having a cavity; in a second step clamping the shielding plate between the first corepin and a second corepin of the mold tool; in a third step injecting plastic into the cavity so as to fill the cavity, and in a fourth step retracting the second corepin to create a void and subsequently injecting more plastic so as to fill the void.

Preferably during the first step, positioning of the shielding plate on the first corepin is by means of the bent portion, and is maintained by means of the bent portion in the subsequent steps. The bent portion may have an inner diameter suitably sized to fit around the outer diameter of the lower face of the first corepin.

BRIEF DESCRIPTION OF THE DRAWINGS

The foregoing and further features and advantages of the invention will become apparent from the following description of example embodiments with reference to the accompanying figures, wherein like numerals are used to represent like elements and wherein:

FIG. 3a is a view showing the first step of a method for insert molding a shielding plate with a lower housing of the access port according to the invention;

FIG. 3b is a view showing the second step of the method for insert molding the shielding plate into the lower housing of the access port according to the invention;

FIG. 3c is a view showing the third step of the method for insert molding the shielding plate into the lower housing of the access port according to the invention;

FIG. 3d is a view showing the fourth step of the method for insert molding the shielding plate into the lower housing of the access port according to the invention;

DETAILED DESCRIPTION

Hereinafter, embodiments of the invention will be described in detail with reference to the accompanying drawings.

First Embodiment

A first embodiment of the invention is described in the following.

Figure 1A:
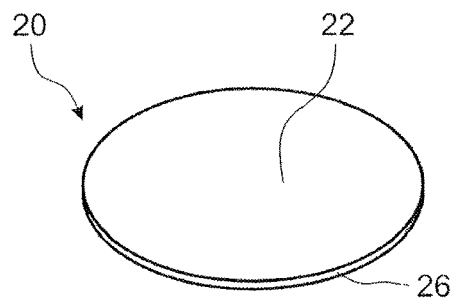
FIG. 1a is a perspective view of a shielding plate of an access port according to the first embodiment.
Figure 1B:
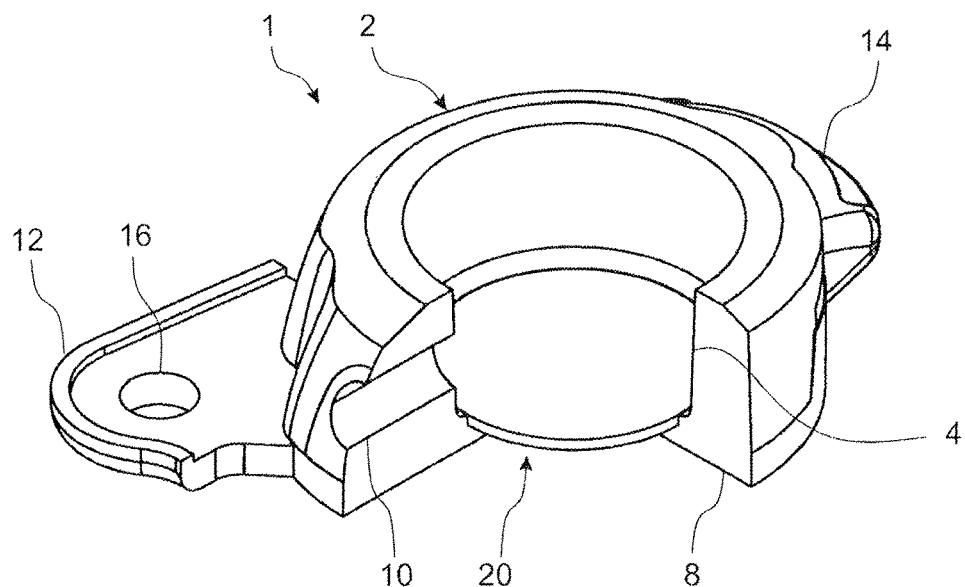
FIG. 1b is a sectional perspective view of a lower housing of the access port according to the first embodiment.
Figure 1C:
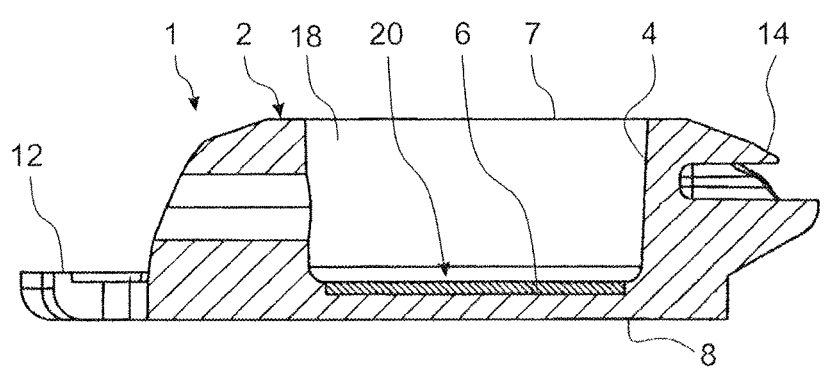
FIG. 1c is a sectional view of the lower housing of the access port according to the first embodiment.

FIG. 1a is a perspective view of a shielding plate 20. FIG. 1b is a perspective sectional view of a lower housing 2 of an access port 1 (cf. FIG. 6a) comprising the shielding plate 20, wherein the shielding plate 20 is shown unsectioned and the lower housing 2 is shown sectioned. FIG. 1c is a sectional view of the access port 1. The access port 1 has a one-piece lower housing 2 preferably made from molded plastic. A plurality of lugs 12, 14 is integrally formed on the outer surface of the lower housing 2. Preferably the lugs 12, 14 are provided in a triangular arrangement around the lower housing 2, wherein the third lug is not shown in the figures. Suture holes 16 are provided as openings which each extend through a respective lug. The suture holes 16 enable the surgeon, during the implantation procedure, after making an incision in the patient's skin, to fix the lower housing 2 of the access port 1 to the patient's flesh. The lower housing 2 has an external bottom 8, which is preferably planar, and a wall 4. An inner base 6 is arranged at one end of the wall 4. The inner base 6 and wall 4 together form a recess having an open end 7. The inner surface of the wall 4 is preferably cylindrically tapered so that its diameter decreases in a direction towards the inner base 6. The inner base 6 is preferably parallel to the external bottom 8 of the lower housing 2.

A shielding plate 20 which is a disc-shaped member comprising a circular portion 22 is arranged on the inner base 6 of the lower housing 2 such that one face of the shielding plate 20 almost entirely, preferably entirely, covers the inner base 6. The shielding plate 20 has a periphery 26. The shielding plate 20 is preferably made from a hard material such as titanium, stainless steel, or ceramic, and further preferably made from sheet or plate. In the present embodiment the shielding plate 20 has uniform thickness.

A septum (not shown) is arranged at the open end 7 of the recess so as to seal the open end 7. The septum is preferably made from a self-sealing, needle-penetrable material such as silicone. The wall 4, shielding plate 20 and inner surface of the septum together define a reservoir 18.

An exit passage 10 formed in the lower housing 2 laterally penetrates the wall 4 of the reservoir 18. In this way the reservoir 18 is fluidly connected to the outside of the access port 1. A connector or cannula 11 (cf. FIGS. 6a and 6b) is attached and fluidly connected to the exit passage 10 such as by means of a compression fitting arrangement, shown for example in DE 3628337 C2, or by any other suitable means known to the skilled person.

As shown in FIGS. 1b and 1c, the shielding plate 20 is embedded into the inner base 6. That is to say a space corresponding to the shape of the shielding plate 20 is provided in the inner base 6, that accommodates the shielding plate 20. The upper side of the shielding plate 20 is exposed to the reservoir 18 and is flush with the bottom (closed end) of the reservoir 18. The lower side and the periphery 26 of the shielding plate 20 are embedded into the inner base 6 of the lower housing 2. The above-mentioned surfaces are in surface contact with the lower housing 2, thus providing a form-locking connection between shielding plate 20 and lower housing 2.

The advantages of the shielding plate 20 according to the first embodiment are described in the following.

The shielding plate 20 according to the first embodiment has uniform thickness and a simple shape that may be made from plate or sheet. Due to its simple construction, the manufacture of the metal parts of the access port 1 is facilitated compared to an access port that is all-metal or has an all-metal reservoir 18. Therefore a simple design is achieved and manufacturing effort is reduced, while protecting the inner base 6 from needle marks.

The shielding plate 20 of the present embodiment is embedded into the inner base 6 of the lower housing 2. In particular the periphery 26 of the shielding plate 20 is surrounded by the inner base 6 of the lower housing 2. Therefore lateral displacement of the shielding plate 20 is prevented both during an insert molding operation and in service. In addition, the lower side of the shielding plate 20 is supported by the inner base 6. Therefore detachment of the shielding plate 20 from the lower housing 2, due to the force of an inserted needle for example, is prevented, and sealing performance of the reservoir 18 is improved.

The shielding plate 20 according to the present embodiment may be assembled to the lower housing 2 by insert molding. During molding, the material of the lower housing 2 contacts the shielding plate 20 in liquid form. When the liquid plastic solidifies, a reliable surface contact between the lower housing 2 and shielding plate 20 is formed, and anchoring of the shielding plate 20 to the lower housing 2 is further ensured here.

In a preferable modification (not shown in the figures) to an insert molded shielding plate 20 according to the first embodiment, the upper side of the circular portion 22 is concave. In this way surface pressure can be applied from the first corepin 30 of a mold tool predominantly towards the outer diameter of the upper face of the shielding plate 20 so as to avoid leakage of liquid plastic past this region and into the reservoir 18 during molding.

Second Embodiment

A second embodiment of the invention is described in the following, wherein the differences from the first embodiment are described.

Figure 2A:
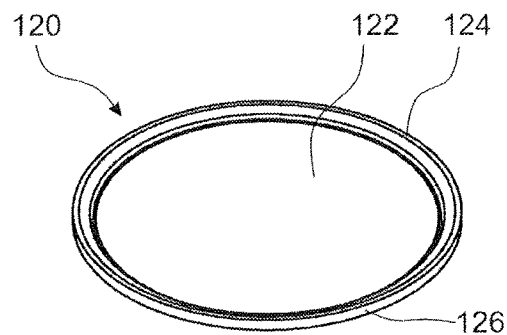
FIG. 2a is a perspective view of a shielding plate of an access port according to a second embodiment.
Figure 2B:
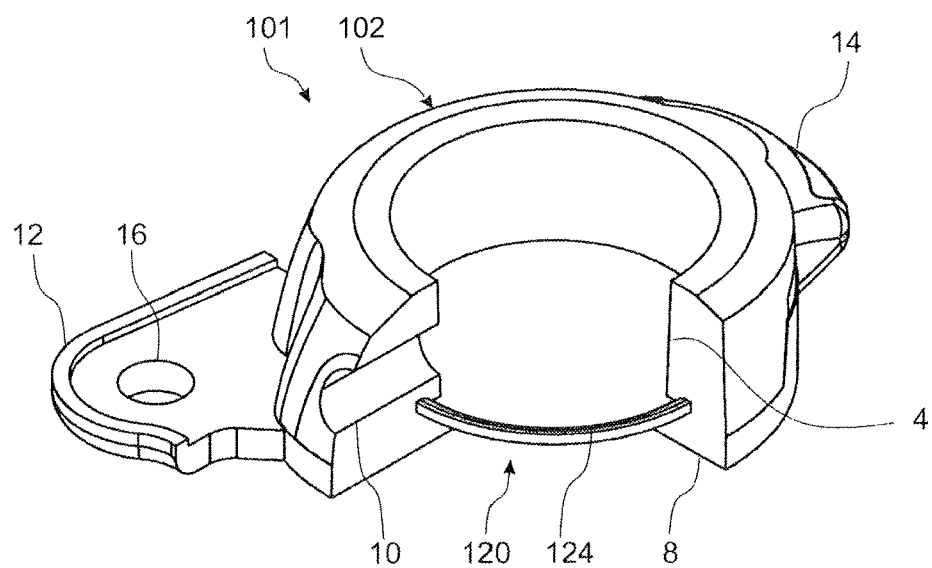
FIG. 2b is a sectional perspective view of a lower housing of the access port according to the second embodiment.
Figure 2C:
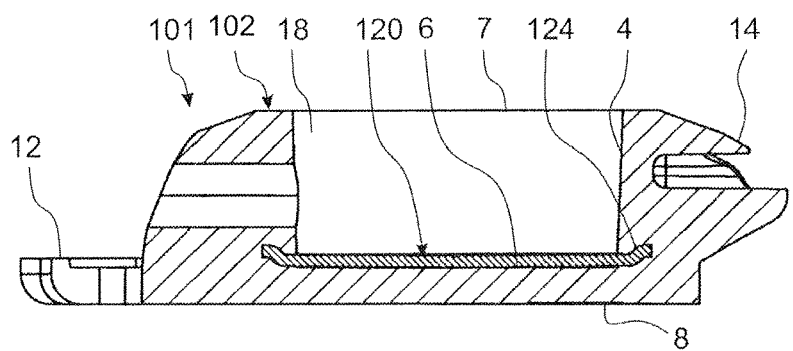
FIG. 2c is a sectional view of the lower housing of the access port according to the second embodiment.

FIG. 2a is a perspective view of a shielding plate 120. FIG. 2b is a perspective sectional view of a lower housing 102 of an access port 101 comprising the shielding plate 120, wherein the shielding plate 120 is shown unsectioned and the lower housing 102 is shown sectioned. FIG. 2c is a sectional view of the access port 101. As shown most clearly in FIG. 2a, the shielding plate 120 has a bent portion 124 provided all around a circular portion 122, and a periphery 126. As shown most clearly in FIG. 2c, the bent portion 124 extends axially upwards and laterally outwards. Thus a circumferential lip is formed on the shielding plate 120. In the present embodiment the shielding plate 120 has uniform thickness. In the case that the shielding plate 120 is made from metal, it may be cut from sheet or plate and bent to the required shape, for example.

As shown in FIGS. 2b and 2c, the shielding plate 120 is preferably integrated with the lower housing 102 by insert molding. The diameter of the shielding plate 120 is greater than the minimum diameter of the wall 4. In this way all sides of the bent portion 124 are embedded into the lower housing 102.

In total the following elements of the shielding plate 120 are embedded into the lower housing 102: the lower side of the shielding plate 120, the periphery 126, and an annular region including all surfaces of the bent portion 124. The elements mentioned above are in surface contact with the lower housing 102, thus providing a form-locking connection between shielding plate 120 and lower housing 102. The remaining region of the upper side of the shielding plate 120 is exposed to the reservoir 18. In addition the shielding plate 120 preferably completely covers the inner base 6 of the reservoir 18.

A preferred method for manufacturing the access port 101 so as to integrate the shielding plate 120 is described below together with FIGS. 3a to 3d.

An insert molding process which is an injection molding process is used to form the lower housing 102 while simultaneously integrating the shielding plate 120, using a mold tool. The main steps of the molding process are shown in FIGS. 3a to 3d, respectively. In these figures the mold tool itself is not shown but corepins 30, 32 of the mold tool are shown.

In a first step (S1) shown in FIG. 3a, the shielding plate 120 is positioned with respect to a cylindrical first corepin 30 of the mold tool, which is a corepin 30 that occupies the space of the reservoir 18 during molding. In order to align the shielding plate 120 with respect to the mold tool, it is positioned concentrically on the first corepin 30, preferably by means of the bent portion 124 which serves here as locating means. The locating effect of the bent portion 124 functions by the bent portion 124 extending laterally beyond the edge of the face of the first corepin 30 and axially along the cylindrical surface of the first corepin 30. Preferably here the bent portion 124 has an inner diameter suitably sized to fit around the outer diameter of the lower face of the first corepin 30.

In a second step (S2) shown in FIG. 3b, two second core pins 32 contact the side of the shielding plate 120, so that the shielding plate 120 is clamped between the first corepin 30 on the upper side and the second corepins 32 on the lower side of the shielding plate 120. The mold tool is then closed to form a cavity.

In a third step (S3) shown in FIG. 3c, plastic is injected into the mold such that at least the majority of the mold cavity is filled.

In a fourth step (S4) shown in FIG. 3d, the second core pins 32 are retracted to be flush with the surrounding mold (that is to say flush with the external bottom 8 of the lower housing 102) so as to create voids. At this point more plastic is injected into the mold so as to fill the voids and thus fill mold entirely. Subsequently the assembly that is the lower housing 102 and the shielding plate 120 can be removed from the mold tool.

As shown in FIG. 3a, the upper side of the circular portion 122 is preferably conical at the start of step S1. In this way, in step S2, the first corepin 30 presses on the shielding plate 120 biased by means of its conical shape, that is to say the surface pressure applied to the circular portion 122 increases laterally. In this way an axial clearance is formed in step S1 between a central region of the shielding plate 120 and a central region of the first corepin face. Thus as the first corepin 30 is brought towards the second corepins 32 in step S2, the first corepin 30 contacts a laterally outer annular region of the shielding plate before a laterally inner region. In FIG. 3b (step S2) the shielding plate 120 is preferably pushed flat, i.e. the first corepin 30 and second corepins 32 are pressed together to flatten the circular portion 122.

In addition to the advantages of the first embodiment, the advantages of the shielding plate 120 according to the second embodiment are described in the following.

In the present embodiment an annular region of the shielding plate 120 including all surfaces of the bent portion 124 is embedded into the wall 4. In addition the lower side of the shielding plate 120 is embedded into the inner base 6. As a result the shielding plate 120 cannot loosen axially into the direction of the reservoir 18. Therefore the form-locking connection between the shielding plate 120 and lower housing 102 is further improved. Also a leak path from the reservoir 18 to the underside of the shielding plate 120 is prevented.

The bent portion 124 extends in an axial direction. As a result it is prevented that the shielding plate 120 can come loose from the wall 4 in a lateral direction. The anchoring of the shielding plate 120 in the lower housing 102 is further ensured.

The shielding plate 120 has a bent portion 124. During molding of the lower housing 102, the bent portion 124 may serve to centre the shielding plate on the first corepin 30 of the mold, the axial extension of the bent portion 124 preventing lateral movement of the shielding plate 120 during the molding process. Therefore the accuracy of location of the shielding plate 120 with respect to the lower housing 102 is improved and the manufacture of the access port 101 is facilitated.

The upper side of the circular portion 122 (i.e. the side facing the first corepin 30) is preferably concave at the start of step S1. When the second corepins 32 press the shielding plate 120 against the first corepin 30 in step S2, the sealing of the shielding plate 120 to the upper core pin 30 at the shielding plate's annular and laterally outer region on its upper side is improved. Therefore the likelihood of plastic leaking between the first corepin 30 and circular portion 122 of the shielding plate 120 is reduced.

Third Embodiment

A third embodiment of the invention is described in the following, wherein the differences from the second embodiment are described.

Figure 4A:
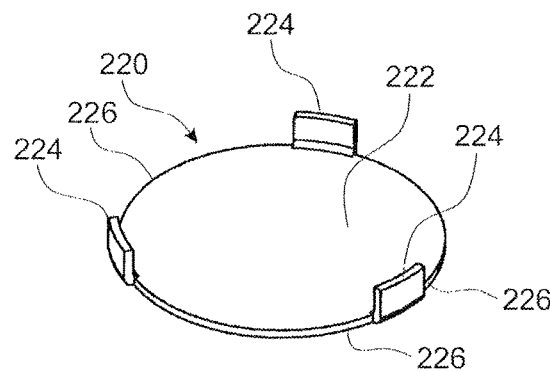
FIG. 4a is a perspective view of a shielding plate of an access port according to a third embodiment.
Figure 4B:
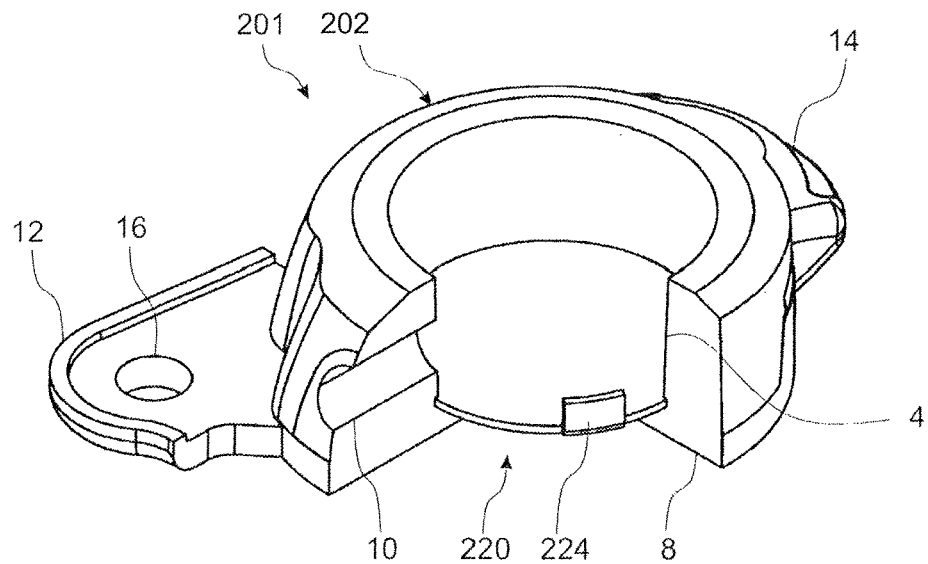
FIG. 4b is a sectional perspective view of a lower housing of the access port according to the third embodiment.
Figure 4C:
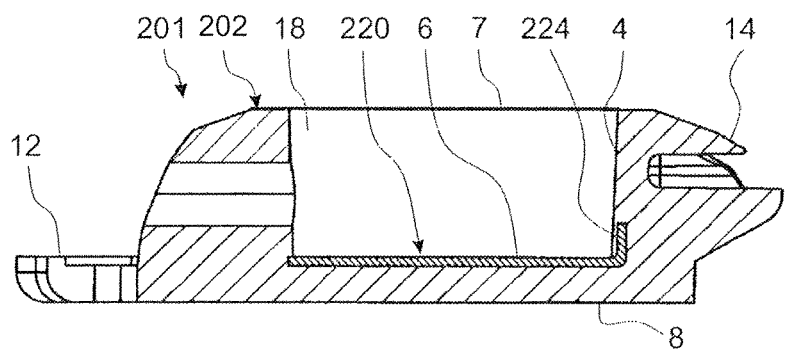
FIG. 4c is a sectional view of the lower housing of the access port according to the third embodiment.

FIG. 4a is a perspective view of a shielding plate 220. FIG. 4b is a perspective sectional view of lower housing 202 of an access port 201 comprising the shielding plate 220, with the shielding plate 220 shown unsectioned and lower housing 202 shown sectioned. FIG. 4c is a sectional view of the access port 201. As shown most clearly in FIG. 4a, the shielding plate 220 has a bent portion 224 in the form of three extensions 224 that are arranged on and spaced around the periphery 226 of the circular portion 222.

As shown in FIGS. 4b to 4c, the shielding plate 220 is integrated with the lower housing 202, preferably by insert molding. As shown most clearly in FIG. 4c, the diameter of the circular portion 222 is greater than the diameter of the wall 4 where the wall 4 meets the inner base 6. In this way an annular region of the upper side of the circular portion 222 as well as all sides of each extension 224, are embedded into the lower housing 202.

In total the following elements of the shielding plate 220 are embedded into the lower housing 202: the lower side of the circular portion 222; the periphery 226; an annular region of the upper side of the circular portion 222, and all the surfaces of each extension 224. The elements mentioned above are in surface contact with the lower housing 202, thus providing a form-locking connection between shielding plate 220 and lower housing 202. The remaining region of the upper side of the shielding plate 220 is exposed to the reservoir 18. The shielding plate 220 preferably completely covers the inner base 6 of the reservoir 18.

Each extension 224 is suitably sized with respect to the lower housing 202 so as not to obstruct the exit passage 10. Preferably the extensions 224 have the same thickness as the circular portion 222.

The steps of the insert molding process described above for the second embodiment and shown in FIGS. 3a to 3d are applicable to the shielding plate 220 according to the third embodiment.

In the case of insert molding, in the first molding step S1 the shielding plate 220 is positioned with respect to the first corepin 30 such that each extension 224 extends axially along the cylindrical surface of the first corepin 30. Preferably here each extension 224 has an inner lateral dimension suitably sized to fit around the outer diameter of the lower face of the first corepin 30. In this way axial alignment of the shielding plate 220 with respect to the first corepin 30 is facilitated. In order to ensure a sufficient locating effect, the extensions 224 are equispaced around the periphery 126 of the circular portion 222.

In addition to the advantages of the first embodiment, the advantages of the shielding plate 220 according to the third embodiment are described in the following.

The shielding plate 220 has three axially extending extensions 224 embedded into the lower housing 202. As a result it is further prevented that the shielding plate 220 can come loose from the wall 4 in a lateral direction. Therefore a stronger form-locking connection between the shielding plate 220 and lower housing 202 is achieved and the anchoring of the shielding plate 220 is further improved.

In the case that the shielding plate 220 is made from bent sheet, the bending of the extensions 224 requires less effort than bending of the entire periphery of the shielding plate 120 of the second embodiment.

The shielding plate 220 according to the third embodiment has three axially extending extensions 224. During molding of the lower housing 202, the extensions 224 may serve to centre the shielding plate 220 on the first corepin 30 of the mold, preventing lateral movement and providing a clearer visual indication that the shielding plate 220 is correctly seated on the first corepin 30. Therefore the accuracy of location of the shielding plate 220 within the lower housing 202 is further improved and the manufacture of the access port 201 is further facilitated.

The respective axial length of each extension 224 may be suitably sized so as not to obstruct the exit passage 10 when any one of the extensions 224 is aligned with the exit passage 10. Therefore an arbitrary orientation of the shielding plate 220 with respect to the lower housing 202 is possible.

Fourth Embodiment

A fourth embodiment of the invention is described in the following, wherein the differences from the first embodiment are described.

Figure 5A:
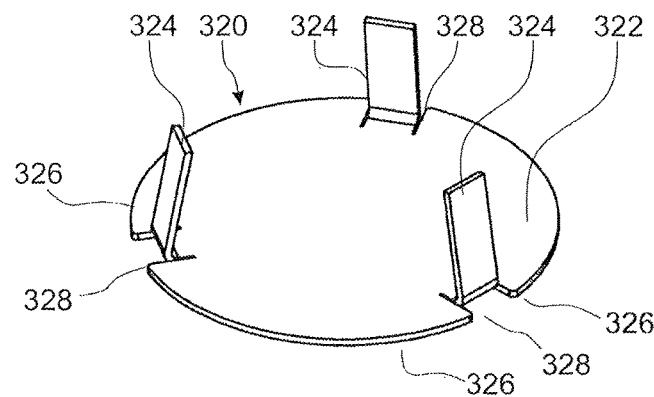
FIG. 5a is a perspective view of a shielding plate of an access port according to a fourth embodiment.
Figure 5B:
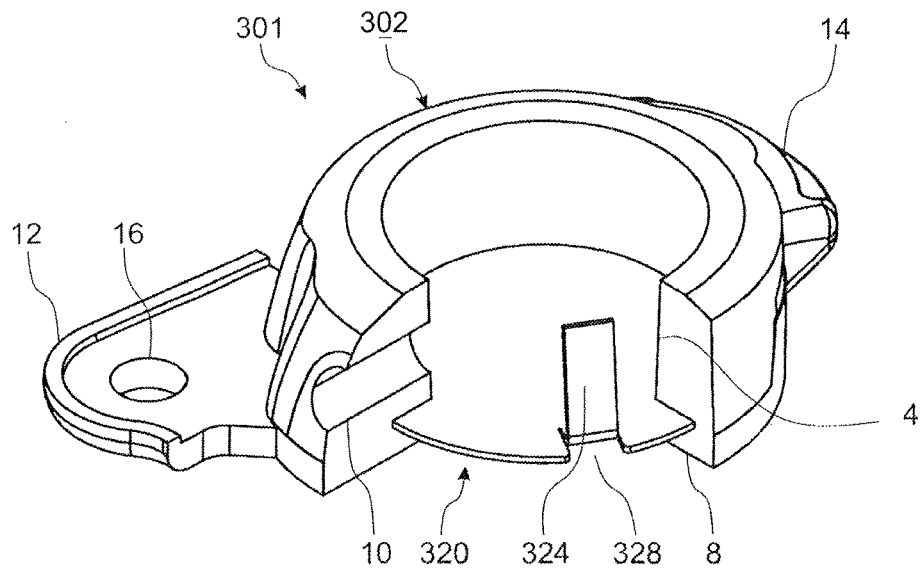
FIG. 5b is a sectional perspective view of a lower housing of the access port according to the fourth embodiment.
Figure 5C:
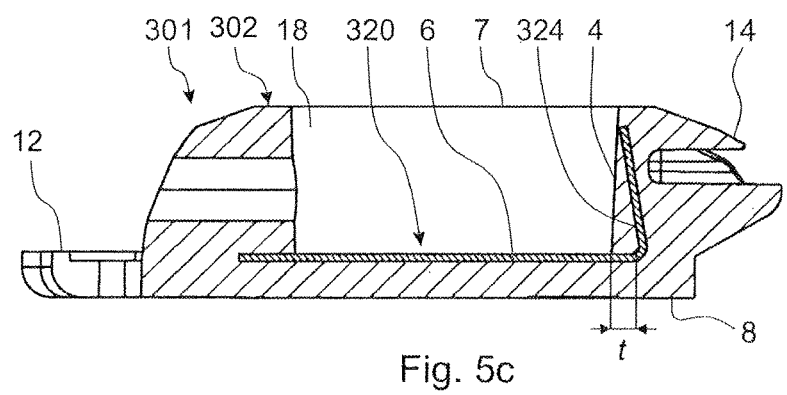
FIG. 5c is a sectional view of the lower housing of the access port according to the fourth embodiment.

FIG. 5a is a perspective view of a shielding plate 320. FIG. 5b is a perspective sectional view of a lower housing 302 of an access port 301 comprising the shielding plate 320, with the shielding plate 320 shown unsectioned and an lower housing 302 shown sectioned. FIG. 5c is a sectional view of the access port 301. The shielding plate 320 has a bent portion 324 in the form of three long extensions 324 that are arranged in a circular pattern on the circular portion 322, each long extension 324 extending along the majority of the axial length of the wall 4. The long extensions 324 are resiliently laterally deformable. Furthermore each long extension 324 in its free state is inclined toward the axis of the reservoir 18, as can be seen most clearly in FIG. 5c. In the present embodiment the lateral extent of each long extension 324 is less than the lateral extent of the circular portion 322. In other words the diameter of the periphery 326 is preferably greater than the lateral extent of each long extension 324. In addition the diameter of the periphery 326 of the circular portion 322 is preferably greater than the maximum internal diameter of the reservoir 18. As a result recesses 328, each having the same angular position as a respective long extension 324, are formed on the periphery of the circular portion 122. The recesses 328 allow the plastic wall thickness of the wall 4 to be locally increased at the recesses 328 so as to be uninterrupted by the shielding plate 320.

In total the following elements of the shielding plate 320 are embedded into the lower housing 302: the lower side of the circular portion 322; the periphery 326; an annular region of the upper side of the circular portion 322, and all the surfaces of each long extension 324. The elements mentioned above are in surface contact with the lower housing 302, thus providing a form-locking connection between shielding plate 320 and lower housing 302. The remaining region of the upper side of the shielding plate 320 is exposed to the reservoir 18. The shielding plate 320 preferably completely covers the inner base 6 of the reservoir 18.

Preferably an orientation of the shielding plate 320 is chosen such that none of the long extensions 324 obstructs the exit passage 10.

The steps of the insert molding process described above for the second embodiment and shown in FIGS. 3a to 3d are applicable to the shielding plate 320 according to the fourth embodiment.

In the case of insert molding, in the first molding step S1 the shielding plate 320 is positioned with respect to the first corepin 30, preferably with each long extension 324 extending along the cylindrical surface of the first corepin 30 so that the shielding plate 320 is axially aligned with respect to the first corepin 30. Preferably here each long extension 324 has a minimum lateral dimension suitably sized to fit around the outer diameter of the lower face of the first corepin 30. In doing so, each long extension 324 contacts, and is preferably also biased against, the cylindrical surface of the first corepin 30. In order to ensure a sufficient locating effect, the long extensions 324 are preferably equispaced on the circular portion 322.

In addition to the advantages of the third embodiment, the shielding plate 320 according to the fourth embodiment has the following further advantages.

The shielding plate 320 has three long extensions 324 that are arranged in a circular pattern on the circular portion 322, each extending over the majority of the axial length of the wall 4. In addition the diameter of the periphery 326 of the circular portion 322 is preferably greater than the maximum internal diameter of the reservoir 18. As a result it is even further prevented that the shielding plate 320 can come loose from the wall 4 in a lateral or axial direction. In particular axial displacement of the shielding plate is further prevented. Therefore an even stronger form-locking connection between the shielding plate 320 and lower housing 302 is achieved and the anchoring of the shielding plate 320 is even further improved.

In the present embodiment, recesses 328 are formed on the periphery 326 of the circular portion 322, which allow the uninterrupted plastic wall thickness of the wall 4 to be locally increased at these positions. In other words the plastic material of the wall 4 is allowed to extend through and laterally beyond each recess 328. Therefore the overall strength of the wall 4 is maintained even when the diameter of the periphery 326 of the circular portion 322 is greater than the maximum internal diameter of the reservoir 18. In other words reinforcing portions are created within the wall and the wall 4 is not excessively weakened by the embedding of part of the circular portion 322.

Due to the provision of the recesses 328, the lateral extent of each long extension 324 can be less than the diameter of the circular portion 322. Therefore the choice of diameter of the circular portion 322 is unconstrained by the positional requirements of the long extension.

Each long extension 324 is inclined toward the axis of the reservoir 18. As a result the wall thickness (marked "t" in FIG. 5c) on the radially inner side of each the long extension 324 increases in an axial direction from the open end 7 towards the reservoir 18. Therefore the strength of the wall 4 is increased at the inner base 8 end, without the long extensions 324 interfering with the external features of the housing at the open end side such as the lug 14.

The shielding plate 320 according to the fourth embodiment may be assembled to the lower housing 302 by the insert molding process described above. The long extensions 324 may serve to here to align the shielding plate 320 with respect to the first corepin 30 of the mold. Each long extension 324 may be inclined with respect to the cylindrical surface of the first corepin 30 such that only the tips of the long extensions 324 make contact with the first corepin 30. The long extensions 324 may be dimensioned to be biased against the surface of the first corepin 30. In this way axial alignment with the first corepin 30 is improved in comparison with the preceding embodiments because lateral clearance between each long extension 324 and the first corepin 30 is reduced, preferably removed.

Figure 6A:
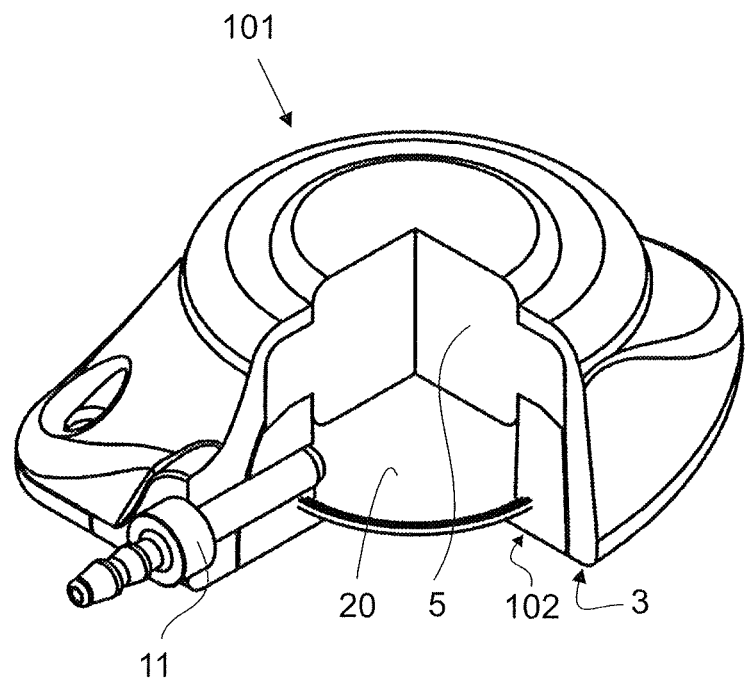
FIG. 6a is a sectional perspective view of the access port according to the second embodiment.
Figure 6B:
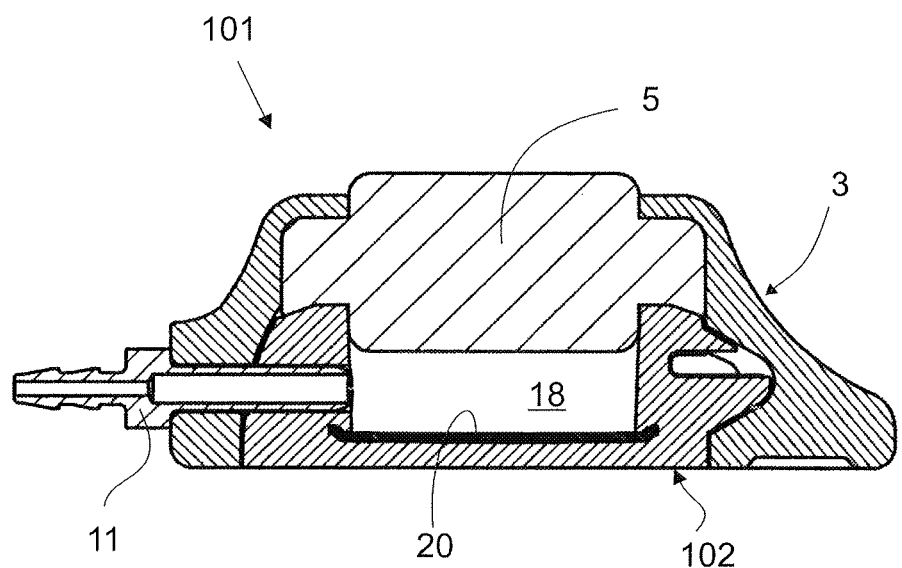
FIG. 6b is a sectional view of the access port according to the second embodiment.

FIGS. 6a and 6b show the entire access port 1. FIG. 6a shows a perspective and partial sectional view of the access port 1 having the lower housing 102 according to the second embodiment and an upper housing 3 that are connected to each other. The lower housing 102 is covered and surrounded by the upper housing 3. A circular septum 5 is sandwiched at circumferential portions thereof between the lower housing 102 and the upper housing 3. The septum 5 slightly protrudes from a central opening 9 provided in the upper housing 3 and is spaced apart from the shield member 120 embedded in the lower housing 102 so as to form the reservoir 18 therebetween. The upper housing 3 is configured to also be attached to or connected with any one of the lower housings 2, 202 and 302 according to the first, third and fourth embodiment.

The invention is not limited to the above-described embodiments and various modifications may be made within the scope of the appended claims.

For example, in the preceding embodiments the access port has a single reservoir 18. However the invention is not limited to single-reservoir access ports and it may be applied to access ports having more than one reservoir.

In the access port 101 according to the second embodiment, the bent portion 124 extends all around the circular portion 122. The bent portion according to the invention may extend around only a portion or portions of the circular portion.

In the third and fourth embodiments of the invention, the extensions 224, 324 are equispaced and the number of extensions 224, 324 provided on the shielding plate 220, 320 is three. The invention is not limited to this number of extensions and in addition the arrangement of extensions is not limited to being equispaced. Furthermore the respective angles that the extensions 224, 324 make with the axial direction may differ.

In the fourth embodiment of the invention, the long extensions 324 extend over the majority of the axial length of the reservoir 18. The invention is not limited to this distance and the long extensions 324 may extend over the entire axial length of the wall 4.

In the fourth embodiment of the invention, the recesses 328 are formed on the periphery 326 of the circular portion 322. The invention is not limited to this configuration and the recesses may be formed within the circular portion 322.

The molding method described above and shown in FIGS. 3a to 3d is applied to the access port 101 according to the second embodiment. However the method described herein may be applied to any of the above embodiments. In the case of insert molding, alignment of the shielding plate 20 on the first corepin 30 may be performed visually for example.

According to the invention, it is possible to provide an access port having a one-piece plastic lower housing, that comprises a shielding plate that is strongly anchored to the housing.

According to a modification of the invention, the upper housing 3 is integrally formed with the lower housing 2, 102, 202, or 302 so as to form a single-unit molded housing in which the shielding plate 20 is embedded.

The invention claimed is:

1. An access port having a molded housing portion forming a reservoir for receiving fluid, said housing portion comprising a shielding plate arranged on an inner base of the housing portion, an open end in which a septum is arranged, an exit passage, and a wall, the shielding plate comprising a circular portion, wherein:
the shielding plate has a lower side that is embedded into the housing portion, an annular region that is embedded on all of its sides into the housing portion, and an upper side that is exposed to the reservoir,
the annular region comprises a bent portion formed on the annular region, the bent portion comprising a first bent section having a concave curvature relative to the upper side of the shielding plate, and a second bent section having a convex curvature relative to the upper side of the shielding plate, and the first bent section and the second bent section form a circumferential lip on the shielding plate, the circumferential lip being embedded into the housing portion in a form-locking connection between the shielding plate and the housing portion.

2. The access port according to claim 1, wherein the shielding plate is metallic or ceramic.

3. The access port according to claim 1, wherein the shielding plate is bonded to the housing portion.

4. The access port according to claim 1, wherein the shielding plate is insert molded into the housing portion.

5. The access port according to claim 1, wherein the bent portion is formed all around the annular region.

6. The access port according to claim 1, wherein a maximum diameter of the shielding plate is greater than a maximum internal diameter of the reservoir.

* * * * *